United States Patent
Healey et al.

(10) Patent No.: US 10,189,150 B2
(45) Date of Patent: Jan. 29, 2019

(54) TORQUE LIMITING LOCKING CAP

(71) Applicant: DEPUY SYNTHES PRODUCTS, INC., Raynham, MA (US)

(72) Inventors: Richard Healey, West Chester, PA (US); Philip Watt, New Holland, PA (US); Adam Nelson, Media, PA (US); Steven Greco, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 190 days.

(21) Appl. No.: 15/061,713

(22) Filed: Mar. 4, 2016

(65) Prior Publication Data

US 2017/0252908 A1 Sep. 7, 2017

(51) Int. Cl.
| | | |
|---|---|---|
| *B25B 23/157* | (2006.01) | |
| *B25B 23/142* | (2006.01) | |
| *A61B 17/88* | (2006.01) | |
| *B25B 23/00* | (2006.01) | |
| *B25B 15/02* | (2006.01) | |
| *B25B 23/14* | (2006.01) | |

(52) U.S. Cl.
CPC ........ *B25B 23/1427* (2013.01); *A61B 17/888* (2013.01); *A61B 17/8875* (2013.01); *B25B 15/02* (2013.01); *B25B 23/0035* (2013.01); *B25B 23/0042* (2013.01); *B25B 23/141* (2013.01)

(58) Field of Classification Search
USPC .......................... 81/467, 474, 475, 478, 480
See application file for complete search history.

(56) References Cited

U.S. PATENT DOCUMENTS

| | | | |
|---|---|---|---|
| 2,300,652 A | | 11/1942 | Cooney |
| 2,396,040 A | | 3/1946 | Darling |
| 2,919,602 A | * | 1/1960 | Spraragen ................ F16D 7/10 464/35 |
| 4,466,523 A | * | 8/1984 | De Carolis ........... B25B 13/462 192/43.1 |
| 4,838,264 A | | 6/1989 | Bremer et al. |

(Continued)

FOREIGN PATENT DOCUMENTS

| | | |
|---|---|---|
| WO | 2014/159027 A1 | 10/2014 |
| WO | 2015/153376 A1 | 10/2015 |

OTHER PUBLICATIONS

Communication relating to the Results of the Partial International Search, for PCT/US2017/020475 dated May 24, 2017.

(Continued)

*Primary Examiner* — Joseph J Hail
*Assistant Examiner* — Shantese McDonald
(74) *Attorney, Agent, or Firm* — Kramer Amado, P.C.

(57) ABSTRACT

A torque limiting driver system, including: a torque limiting driver including: a handle with a locking cap engagement protrusion; a shaft with a cam portion including a cam mating feature; and a locking cap including: a mating recess including a plurality of scallops along the outer edge of the mating recess and wherein the plurality of scallops are configured to interface with the first mating feature; a through-hole with through-hole mating feature configured to interface with the cam mating feature, wherein the locking cap is configured to engage the torque limiting driver to lock the rotation of the shaft with respect to the handle.

4 Claims, 9 Drawing Sheets

(56) References Cited

U.S. PATENT DOCUMENTS

| | | | | |
|---|---|---|---|---|
| 5,535,648 | A * | 7/1996 | Braun | B25B 13/462 |
| | | | | 81/60 |
| 6,095,020 | A * | 8/2000 | Rinner | B25B 15/02 |
| | | | | 81/475 |
| 6,216,570 | B1 * | 4/2001 | Freed | A61B 17/8894 |
| | | | | 81/467 |
| 7,222,559 | B2 * | 5/2007 | Wang | B25B 15/00 |
| | | | | 81/467 |
| 7,487,700 | B2 | 2/2009 | Cutler et al. | |
| 7,762,164 | B2 | 7/2010 | Nino | |
| 7,938,046 | B2 | 5/2011 | Nino | |
| 8,757,035 | B2 | 6/2014 | Kerboul et al. | |
| 9,162,350 | B2 | 10/2015 | Nino et al. | |
| 9,693,814 | B2 * | 7/2017 | Schaller | B25B 23/0042 |
| 2008/0028899 | A1 | 2/2008 | Scott | |
| 2008/0243134 | A1 | 10/2008 | Limberg et al. | |
| 2009/0275994 | A1 * | 11/2009 | Phan | A61B 17/7064 |
| | | | | 606/86 A |
| 2015/0122091 | A1 * | 5/2015 | Chen | B25B 23/1427 |
| | | | | 81/475 |
| 2015/0143966 | A1 | 5/2015 | Pischke et al. | |
| 2016/0038210 | A1 | 2/2016 | Plotkin | |

OTHER PUBLICATIONS

Notification of Transmittal of the International Search Report and Written Opinion of the International Searching Authority, or the Declaration, and International Search Report for PCT/US2017/020475 dated Aug. 21, 2017.

* cited by examiner

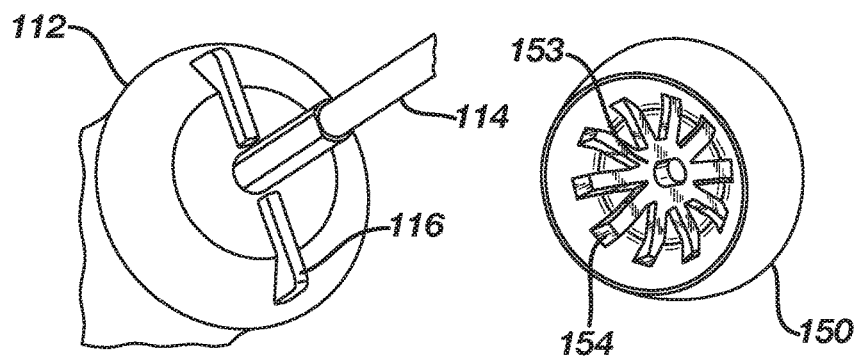
FIG. 4A
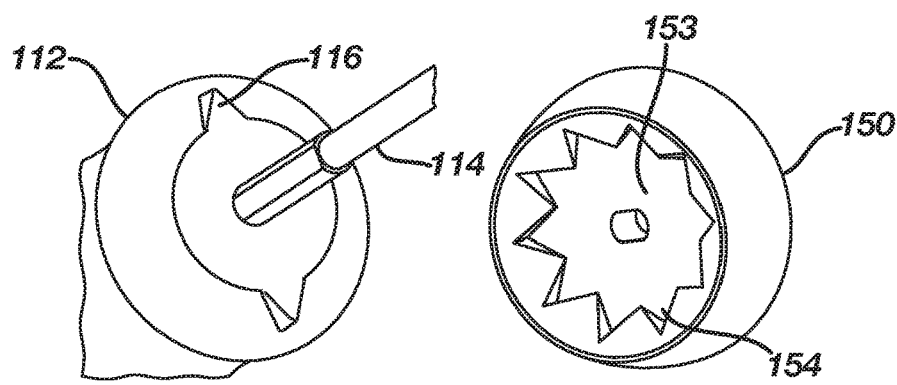
FIG. 4B
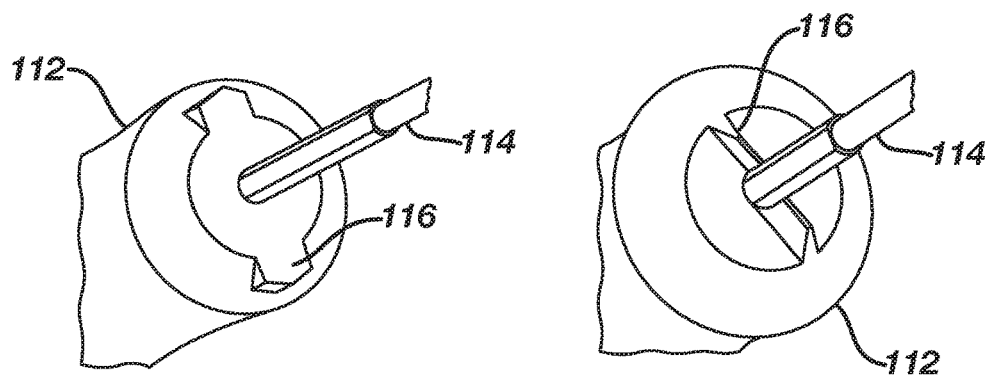
FIG. 4C          FIG. 4D

1

TORQUE LIMITING LOCKING CAP

TECHNICAL FIELD

Various exemplary embodiments disclosed herein relate generally to a torque limiting locking cap.

BACKGROUND

Surgeons use drivers, such as screwdrivers, to drive screws into bones in various surgical procedures. If the surgeon applies too much torque while tightening these screws, the bone may strip. As a result the screw will not be securely held by the bone. Further, if the screw is being used to secure a bone plate, too much torque on the screw may damage the plate or even drive the screw through the plate. Torque limiting drivers may be used to limit the torque to prevent stripping the hole in the bone and to prevent over tightening of the screw that may damage a bone plate. Also, the torque limiting driver may be used to determine that the screws have been tightened sufficiently. This may be accomplished by the surgeon tightening the screw until the torque limiting driver slips indicating that the torque limit has been reached. In one example, a torque limiting driver may limit torque to 0.8 Nm. Other torque limits may be used depending upon the specific procedure, the target site, the condition of the bone, and the size of the screws.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a torque limiting driver system, including: a torque limiting driver including: a handle with a locking cap engagement protrusion; a shaft with a cam portion including a cam mating feature; and a locking cap including: a mating recess including a plurality of scallops along the outer edge of the mating recess and wherein the plurality of scallops are configured to interface with the first mating feature; a through-hole with through-hole mating feature configured to interface with the cam mating feature, wherein the locking cap is configured to engage the torque limiting driver to lock the rotation of the shaft with respect to the handle.

Various embodiments are described wherein the first mating feature is a protrusion from an end of the handle.

Various embodiments are described wherein the first mating feature includes two protrusions from an end of the handle.

Various embodiments are described wherein the locking cap includes a mating recess including a plurality of scallops along the outer edge of the mating recess and wherein the plurality of scallops is the third mating feature.

Various embodiments are described wherein the second mating feature is a portion of the shaft that has a flat portion.

Various embodiments are described wherein the fourth mating feature has a flat portion complementary to the flat portion of the second mating feature.

Various embodiments are described wherein: the shaft includes a fifth mating feature, and the locking cap includes a sixth mating feature configured to engage the fifth mating feature such that the locking cap is fixed to the torque limiting driver.

Various embodiments are described wherein the fifth mating feature is a recess in the shaft.

Various embodiments are described wherein the sixth mating feature is a snap arm extending from the locking cap that is configured to snap into the shaft recess.

Various embodiments are described further comprising an O-ring in an O-ring recess surrounding the through-hole of the locking cap, wherein the O-ring engages the shaft such that the locking cap is fixed to the torque limiting driver.

Various embodiments are described further comprising a canted coil spring in a canted coil spring recess surrounding the through-hole of the locking cap, wherein the canted coil spring is configured to engage a shaft recess in the shaft such that the locking cap is fixed to the torque limiting driver.

Various embodiments are described wherein the locking cap further includes a screw hole extending from an outer edge of the locking cap to the through-hole and a screw spring plunger in the screw hole extending to the through-hole, wherein the screw spring plunger is configured to engage a shaft recess in the shaft such that the locking cap is fixed to the torque limiting driver.

Various embodiments are described wherein the locking cap further includes external clips extending from an outer edge of the locking cap wherein the external clips are configured to engage the handle such that the locking cap is fixed to the torque limiting driver.

Further various embodiments relate to a torque limiting driver system, including: a torque limiting driver including: a handle with a locking cap engagement protrusion; a shaft with a cam portion including a cam mating feature; and a locking cap including: a mating recess including a plurality of scallops along the outer edge of the mating recess and wherein the plurality of scallops are configured to interface with the first mating feature; a through-hole with through-hole mating feature configured to interface with the cam mating feature, wherein the locking cap is configured to engage the torque limiting driver to lock the rotation of the shaft with respect to the handle.

Further various embodiments relate to a locking cap for engagement with a torque liming driver including a handle with a first mating feature and a shaft with a second mating feature, including: a third mating feature configured to interface with the first mating feature; and a through-hole with a fourth mating feature configured to interface with the second mating feature, wherein the locking cap is configured to engage the torque limiting driver to lock the rotation of the shaft with respect to the handle.

Is contemplated that various combinations of the embodiments described herein may be made resulting in additional embodiments that are within the scope of the invention described herein.

BRIEF DESCRIPTION OF THE DRAWINGS

In order to better understand various exemplary embodiments, reference is made to the accompanying drawings, wherein:

FIGS. 4A, 4B, 4C, and 4D illustrate alternative embodiments of scallops and locking cap engagement protrusions;

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i e, and/or), unless otherwise indicated (e.g., "or else" or "or in the alternative"). Also, the various embodiments described herein are not necessarily mutually exclusive, as some embodiments can be combined with one or more other embodiments to form new embodiments.

When using torque limiting drivers to drive screws into bone, surgeons sometimes encounter bone that is denser than expected and this may lead to requiring a torque to drive the screw that exceeds the torque limit of the torque limiting driver. In these situations, the surgeon may instead use a normal driver that does not include a torque limiting feature. This leads to various problems. In cost sensitive applications, requiring two drivers adds cost and complexity. Further, it can lead to the surgeon inadvertently using the normal driver and accidently applying to much torque to a screw leading to bone damage. Also, if the normal driver is in another sterile kit, it means opening and wasting another sterile kit. Accordingly, there remains a need to find a solution where a torque limiting driver may be locked when torque greater than the torque limit is needed.

Below embodiments of a torque locking cap are described. The locking cap is a removable device that slides on to the shaft of the driver and mates with the shaft and handle of the torque limiting driver to prevent the rotation of the shaft relative to the handle when the torque limit is exceeded. Further, the locking cap may be held in place using various structures and methods that will be described below.

Figure 1A:
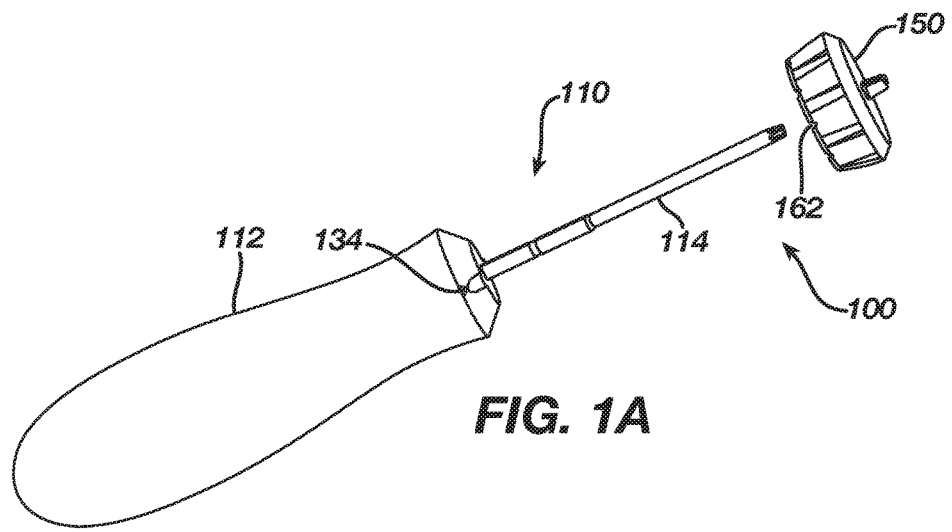
FIGS. 1A, 1B, and 1C illustrate an embodiment of a torque limiting driver system with a driver and a locking cap in various positions.
Figure 1B:
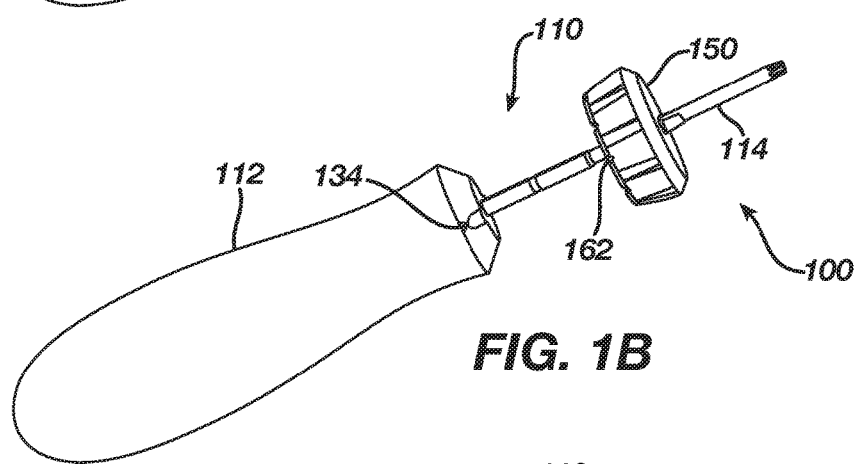
Figure 1C:
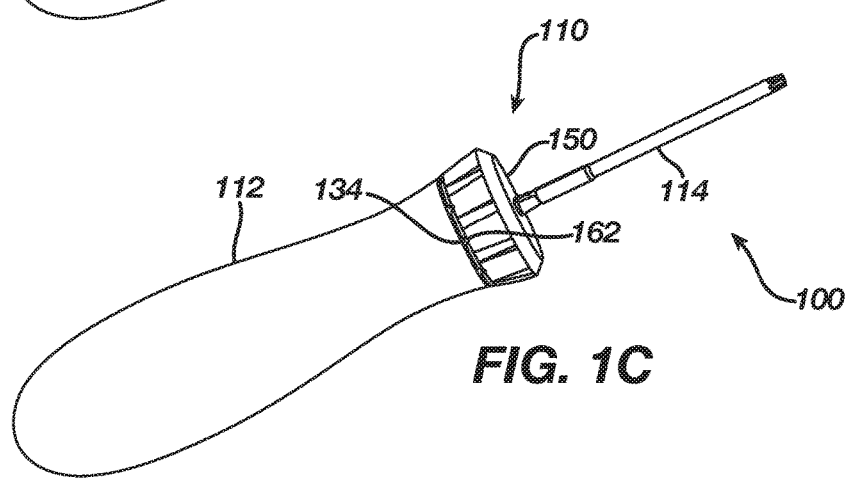

FIGS. 1A, 1B, and 1C illustrate an embodiment of a torque limiting driver system with a driver and a locking cap in various positions. The torque driver system 100 includes a driver 110 and the locking cap 150. The driver 110 may include a handle 112 and a shaft 114 which will be described further below. In FIG. 1A, the locking cap 150 is shown separate from the driver 110. In FIG. 1B, the locking cap 150 has been slid onto the shaft 114. In FIG. 1C, the locking cap 150 has been slid into engagement with the driver 110.

Figure 2A:
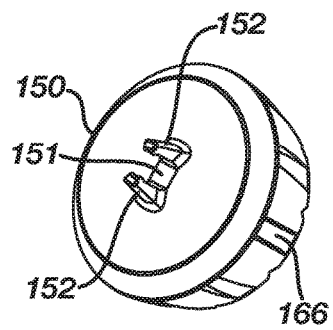
FIGS. 2A and 2B are perspective views of the locking cap.
Figure 2B:
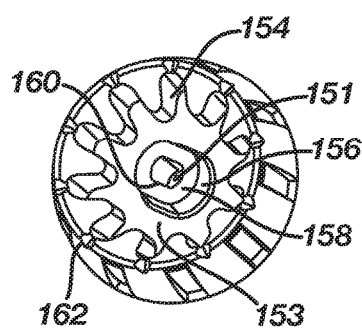
Figure 2C:
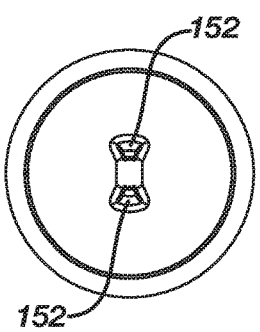
FIG. 2C is top view of the locking cap.
Figure 2D:
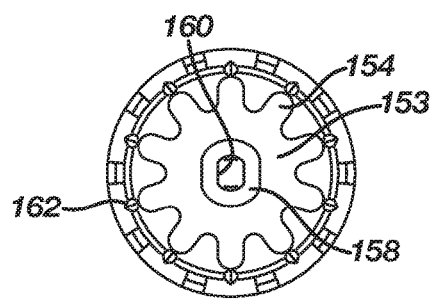
FIG. 2D is a bottom view of the cap.
Figure 2E:
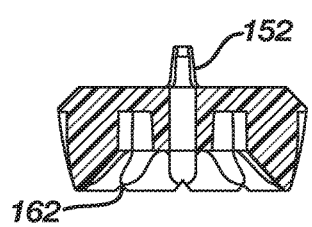
FIGS. 2E and 2F are cross-sectional views of the locking cap.
Figure 2F:
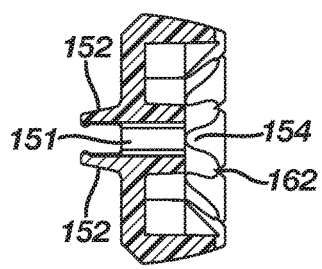
Figure 2G:
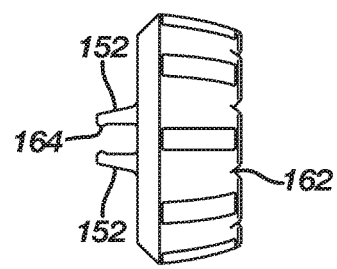
FIG. 2G is a side view of the locking cap.

FIGS. 2A and 2B are perspective views of the locking cap. FIG. 2C is a top view of the locking cap. FIG. 2D is a bottom view of the cap. FIGS. 2E and 2F are cross-sectional views of the locking cap. FIG. 2G is a side view of the locking cap. The locking cap includes a through-hole 151 that is configured to receive the shaft 114 of the driver 110. The top side of the locking cap may include snap arms 152. The snap arms 152 act as a locking cap retainer. The snap arms 152 extend outward from the locking cap in the same direction as the through-hole 151. Further, the snap arms 152 arise from the top side of the locking cap 150 on opposite sides of the through-hole 151. At the distal end of the snap arms 152, a snap arm protrusion 164 protrudes from the snap arms 152 in the direction of the shaft 114. The snap arm protrusions 164 may engage a shaft recess 126 in the shaft 114 to secure the locking cap 150 in place during use. The snap arm protrusions 164 may be rounded or have sloped edges to facilitate engagement and disengagement from the shaft recess 126. Further, the snap arms 152 may be configured so that they apply sufficient force upon the shaft 114 so that the locking cap 150 does not easily slide along the shaft when not secured in place by engaging the shaft recess 126. This may prevent the locking cap 150 from inadvertently sliding off of the shaft. In another embodiment, only a single snap arm 164 may be used or more than two snap arms 164 may be used.

Further, as shown in FIGS. 2B and 2D, the locking cap 150 includes a mating recess 153. The mating recess 153 is formed in the bottom side of the locking cap 150. The mating recess 153 includes scallops 154 along its outer edge. As will be described further below, the mating recess 153 engages with an end of the driver 110 to lock the driver 110. A boss 156 is also in the mating recess 153. The boss 156 further defines the through-hole 151. The boss 156 extends axially in a direction along the through-hole 151 and the shaft 114. The boss 156 has a boss end surface 158 that may mate with the end of the handle 112. This mating may provide a stop for the locking cap 150 when engaged with the driver 110. Further, the boss 156 may include a boss mating surface 160 on the inside of the boss 156 to form an outer surface of the through-hole 151. In this embodiment, the boss mating surface 160 includes two flat surfaces that are configured to engage complementary flat surfaces on the shaft 114. This engagement fixes the locking cap 150 to the shaft 114 so that they cannot rotate relative to one another. Thus, the through-hole 151 has two flat surfaces that act as a through-hole mating surface. The boss mating surface 160 and the through-hole 151 may take other shapes that are complementary to the shape of the shaft 114 as will be discussed further below.

The locking cap 150 may also include an external alignment feature 162. Specifically, in FIGS. 2B, 2E, 2F, and 2G the external alignment feature 162 is shown as a triangular notch in the bottom edge of the locking cap 150. Other shapes and locations may be used. The external alignment features 162 are aligned with an alignment protrusion 134 on the handle 112. The alignment protrusion 134 is shown as having a triangular shape that corresponds to the alignment feature 162. Other shapes and locations of for the alignment protrusion 134 may be used. The purpose the external alignment features 162 is to facilitate aligning the scallops 154 with the locking cap engagement protrusions 116 by the user of the torque limiting driver system 100. This allows for easier mating of the locking cap 150 with the driver 110.

The locking cap 150 may also include a plurality of side indents 166. The side indents 166 may be spread around the circumference of the locking cap 150. The side indents 166 provide a griping surface to facilitate mounting and removing of the locking cap 150. As the locking cap may be manufactured using molding methods, the side indents 166 may also provide a benefit of reducing the likelihood of deformation of the locking cap 150 as it cools during manufacture.

Figure 3A:
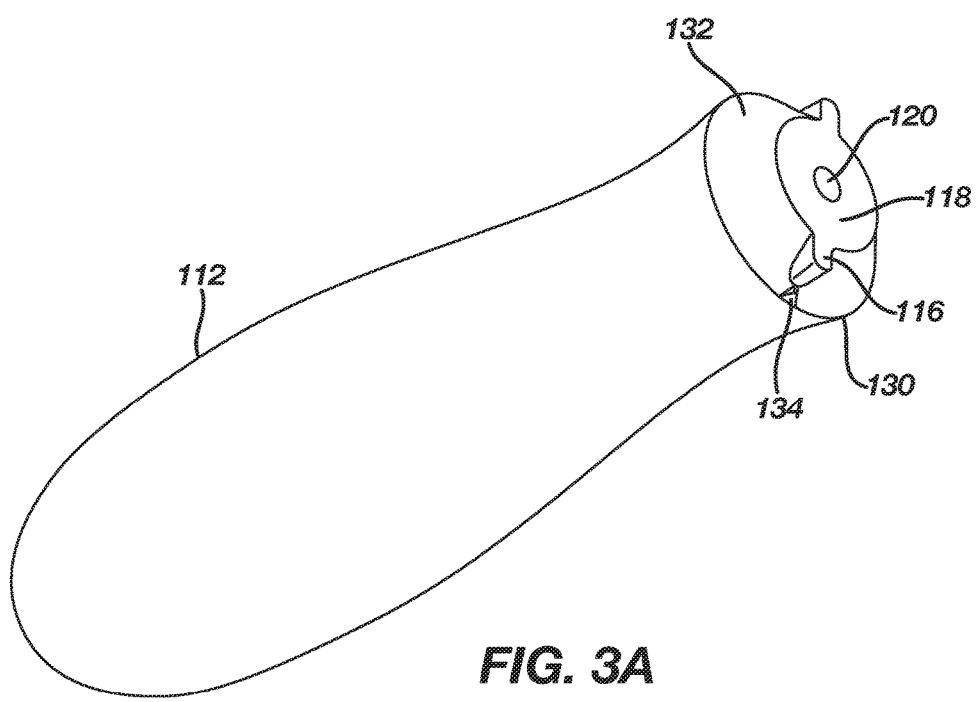
FIG. 3A illustrates the handle of the driver.

FIG. 3A illustrates the handle of the driver. The handle 112 includes locking cap engagement protrusions 116. As shown, there are two locking cap engagement protrusions 116 that extend radially opposite one another. Further, the outer edge of the locking cap engagement protrusions 116 are rounded in complementary manner to the shape of the scallops 154. This facilitates the mating of the handle 112 to the locking cap 150 as the locking cap engagement protrusions 116 fit within and engage the scallops 154. While two locking cap engagement protrusions 116 are illustrated, it is contemplated that one, three or more alignment protrusions 116 may be formed on the handle 112 instead. The locking cap engagement protrusions 116 are shown circumferentially opposite one another, but they could be in any position along the circumference of the handle 112 as long as they are positioned so that each of the locking cap engagement protrusions 116 aligns with the scallops 154. This would also be the case if there are three or more locking cap engagement protrusions 116.

The handle 112 may also include a handle end surface 118. The handle end surface 118 provides a mating surface to the boss end surface 158. The handle end surface 118 also surrounds the handle shaft opening 120. The handle shaft opening 120 accepts the shaft 114.

The handle 112 may include a shoulder 130. Also, the handle 112 may have an end sloped surface 132 that extends from the shoulder 130 to the handle end surface 118. The end sloped surface 132 may be configured to correspond to the general shape of the mating recess 153 in the locking cap 150.

Figure 3B:
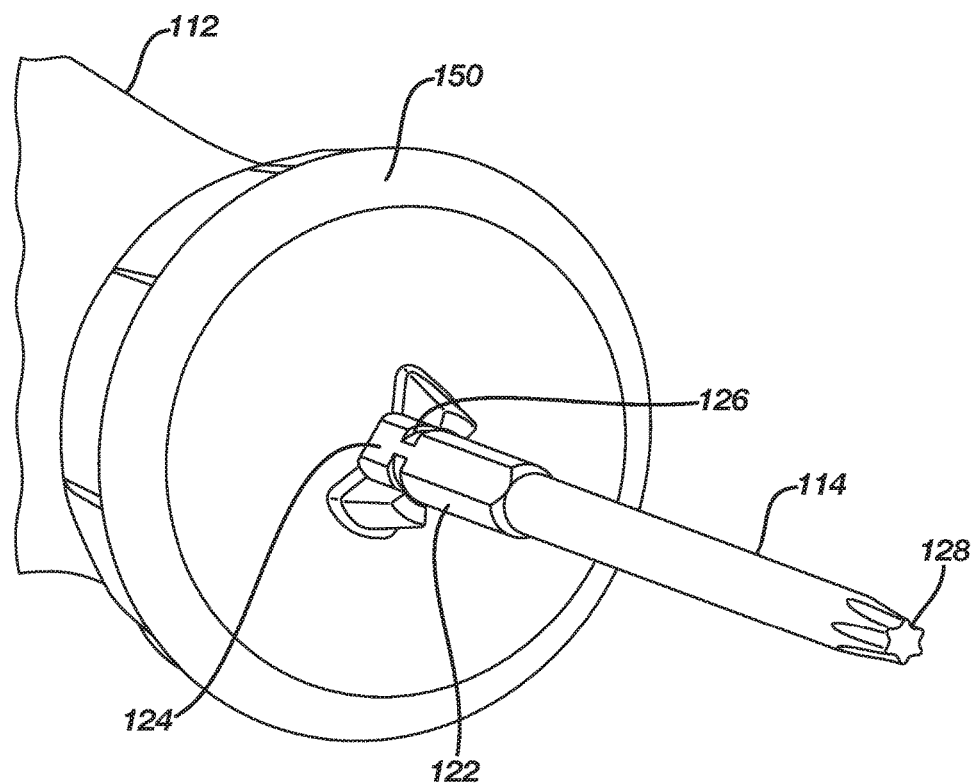
FIG. 3B illustrates a view of the torque limiting driver system with the locking cap mounted on the driver.

FIG. 3B illustrates a view of the torque limiting driver system with the locking cap 150 mounted on the driver 110. The shaft 114 is shown in greater detail. The shaft 114 includes driver head 128 at a distal end of the shaft 114. The driver head 128 is shaped to correspond to the opening in the screw to be driven. In this case the driver head is a torx shape, but any other known driving shape may be used.

The shaft 114 includes cam portion 122. The cam portion 122 is generally larger than the rest of the shaft 114 as shown in FIG. 3B. The cam portion 112 may include a shaft flat portion 124 that acts as a cam mating feature. The circumferential shape of the cam portion 122 corresponds to the shape of the through-hole 151. Thus, the cam portion 122 mates with the through-hole 151 of the locking cap 150 to prevent any relative rotation between the shaft 114 and the locking cap 150. Further, the cam portion 122 may include a shaft recess 126. The shaft recess 126 engages the snap arm protrusions 164 to fix the locking cap 150 in place. This prevents the locking cap 150 from accidently disengaging from the handle 112 while the driver 110 is in use driving screws as well as preventing the locking cap from sliding off of the shaft 114. The shaft recess 126 may have a sloped edge surface to facilitate the disengagement of the snap arms 152 from the shaft recess 126 when the locking cap 150 is disengaged from the driver 110. The shaft recess 126 may extend completely around the cam portion 122 or may just extend partially around the cam portion 122.

The cam portion 122 is shown as round with two flat sections. Other circumferential shapes of the cam portion 122 may be used. For example, the cam portion 122 may be round with one flat, square, hexagonal, or any other shape that prevents rotational slippage between the cam portion 122 and the locking cap 150. The through-hole 151 in the locking cap 150 will have shape that corresponds to the shape of the cam portion 122 in order to prevent relative rotation between the shaft 114 and the locking cap 150. The shapes of the through-hole 151 and the cam portion 112 do not need to be identical to correspond to one another. For example, a square cam portion 112 could be used with a through-hole 151 that is hexagonal or that is round with two flat portions (as shown by the cam portion 112 in FIG. 3B).

The driver 110 includes a torque limiting mechanism (not shown) inside the handle 112. Any known torque limiting mechanism may be used. The torque limiting may have a number of detent positions at angular positions spread out over 360°. When too much torque is applied to the driver 110 the toque limiting mechanism may slip from one detent position to another. The driver 110 may include, for example, ten detent positions in its torque limiting mechanism. Note that the locking cap has ten scallops 154. The number of scallops 154 may equal the number of detents (or an integer number of detents) in the torque limiting mechanism to facilitate the alignment and engagement of the locking cap 150 with the driver 110. The angular location of the detents, locking cap engagement protrusions 116, and the shaft 114 when coupled to the torque limiting mechanism is selected so that when the locking cap 150 is slid onto the cam portion 122, the locking cap engagement protrusions 116 generally align with the scallops 154.

The torque limiting driver system 100 may be used as follows. When a surgeon is driving a screw into dense bone and the torque limiting mechanism prevents the surgeon from further driving the screw before it is completely driven, the surgeon may use the locking cap 150. The surgeon slides the locking cap 150 onto the shaft 114 of the driver 110. As the locking cap 150 slides onto the cam portion 122, the locking cap 150 is rotated so that the shaft flat surface 124 of the cam portion 122 aligns with the boss mating surface 160 in the through-hole 151. The surgeon may align the external alignment feature 162 with a locking cap engagement protrusion 116 to facilitate the alignment of the shaft flat surface 124 of the cam portion 122 with the boss mating surface 160 in the through-hole 151. Once the locking cap 150 is on the cam portion 122, the locking cap 150 may be slid into engagement with the handle 112. Further, the rounded and complementary shapes of the scallops 154 and the locking cap engagement protrusions 116 further facilitate the engagement of the locking cap 150 with the driver 110. When the surgeon has slid the locking cap 150 into contact with the handle 112, the snap arms 152 will snap into the shaft recess 126 to fix the locking cap 150 to the driver 110. With the locking cap 150 engaged, the driver 110 is locked so that the surgeon may finish driving the screw. Once the surgeon is done driving the screw into dense bone, the surgeon may remove the driving cap 150 from the driver 110, thus restoring the torque limiting capability of the driver 110.

In some embodiments, the cap may be slid towards the driver tip 128 without removing the locking cap 150, if the surgeon believes that the locking feature will be required later. This may be accomplished if the snap arms 152 apply sufficient force on the shaft 114 to prevent the locking cap 150 from further sliding. In yet another embodiment, there may be a second shaft recess positioned down the shaft towards the driver tip 128, that may capture the snap arms 152 to fix the locking cap to the shaft 114 in a position where the locking cap 150 is disengaged from the handle 112, and thus restoring the torque limiting capability of the driver 110.

FIGS. 4A, 4B, 4C, and 4D illustrate alternative embodiments of scallops and locking cap engagement protrusions 116. In FIG. 4A the scallops 154 have a generally rectangular shape. The complementary locking cap engagement protrusions 116 have a similar generally rectangular shape. In FIG. 4B the scallops 154 have a generally triangular shape. The complementary locking cap engagement protrusions 116 have a similar generally triangular shape. In FIG. 4C the locking cap engagement protrusions 116 have the illustrated shape. Although not shown, the scallops for this embodiment would have a complementary shape. In FIG. 4D the locking cap engagement protrusions 116 have the illustrated shape where one side is generally perpendicular to the handle end surface 118 and the other side is sloped. Although not shown, the scallops for this embodiment would have a complementary shape. As can be seen by these various embodiments, any shape may be used for the locking cap engagement protrusions 116 and the scallops 154, as long as the shapes are complementary and facilitate engagement that prevents rotation between handle 112 and the shaft 114. Also the shapes should prevent rotational slippage between the locking cap engagement protrusions 116 and the scallops 154 so that the needed torque may be applied by the driver 110 to the screw. Where possible, various edges of the locking cap engagement protrusions 116 may be rounded to reduce or avoid sharp edges. Also, in some embodiments the scallops 154 may be slightly larger than the corresponding locking cap engagement protrusions 116 to facilitate engagement of the locking cap 150.

Figure 5A:
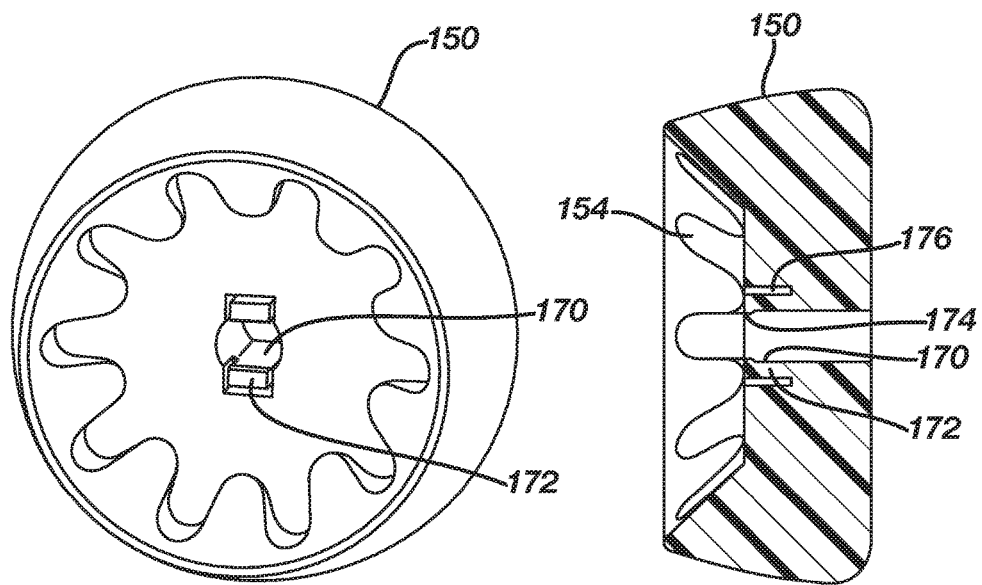
FIGS. 5A, 5B, 5C, 5D, 5E, and 5F illustrate other embodiments of the locking cap.

Various other embodiments for fixing the locking cap 150 to the driver 110 will now be described. FIG. 5A illustrates another embodiment of the locking cap. The locking cap 150 includes internal snap arms 172 with protrusions 174. The protrusions 174 engage a shaft recess 162 to fix the locking cap 150 to the driver 110. The internal snap arms 172 are similar to the snap arms 162 described above. The internal snap arms 172 may have a flat mating surface 170 that defines the through-hole 151 and that mates with the shaft flat surfaces 124. Further, an opening 176 is formed to allow the internal snap arms 170 to flex. A locking cap 150 using internal snap arms 172 may need to be thicker than, for example, the locking cap of FIG. 2A, to allow for a longer through-hole 151 to prevent angular slippage between the locking cap 150 and the cam portion 122.

Figure 5B:
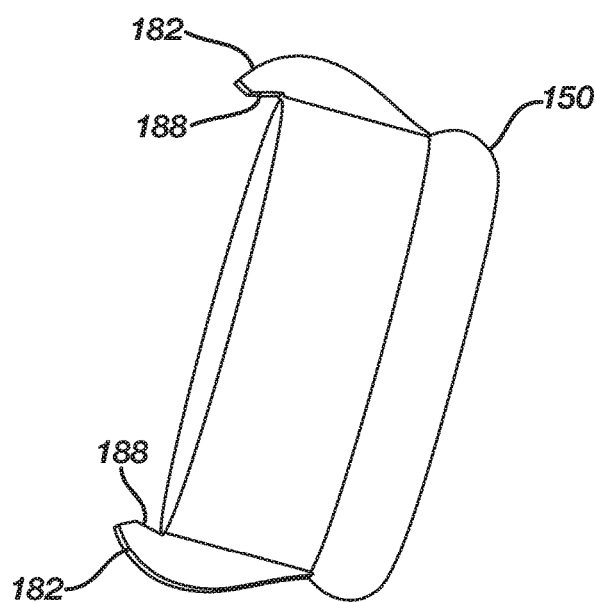

FIG. 5B illustrates another embodiment of the locking cap. The locking cap 150 includes external clips 182. The external clips 182 may be formed on the outer surface of the locking cap 150 and extend in a direction towards the driver 110. The external clips 182 include a sloped portion 188 that slopes back towards a central axis of the locking cap 150. The external clips 182 engage the shoulder 130 of the handle to fix the locking cap 150 to the driver 110.

Figure 5C:
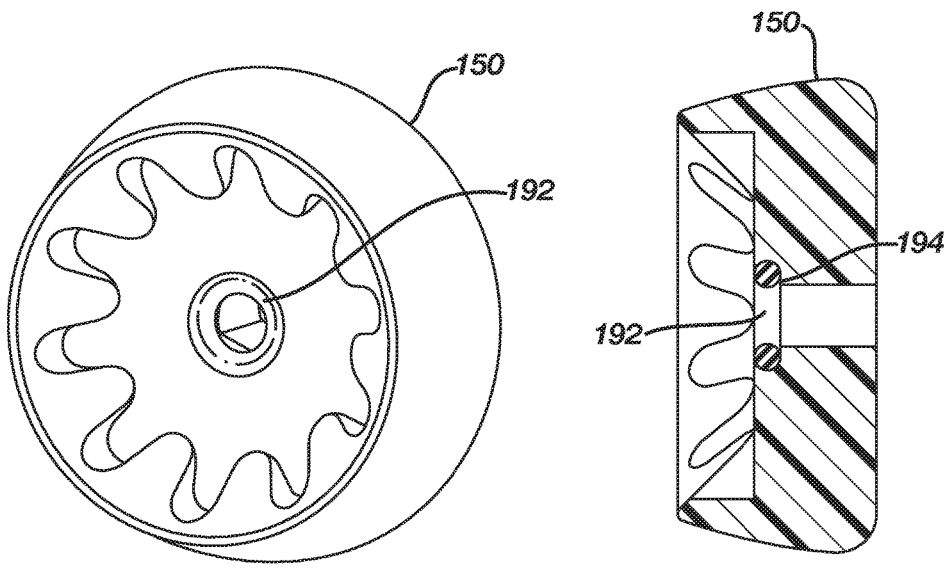

FIG. 5C illustrates another embodiment of the locking cap. The locking cap 150 includes an O-ring 192 in an O-ring recess 194 inside the mating recess 153. The O-ring is configured to engage the cam portion 122 and may provide enough frictional force to fix the locking cap 150 to the driver 110. The O-ring is placed in the O-ring recess 194 to fix the O-ring to the locking cap 150. It is also possible that the O-ring can fix the locking cap 150 in a position where the locking cap 150 does not engage the handle 110 without completely removing the locking cap 150 from the shaft 114. In other embodiments, the O-ring 192 may engage the shaft recess 122 to fix the locking cap 150 to the driver 110. In another embodiment, there may be a second shaft recess to fix the locking cap 150 in a position where the locking cap 150 does not engage the handle 110 without completely removing the locking cap 150 from the shaft 114.

Figure 5D:
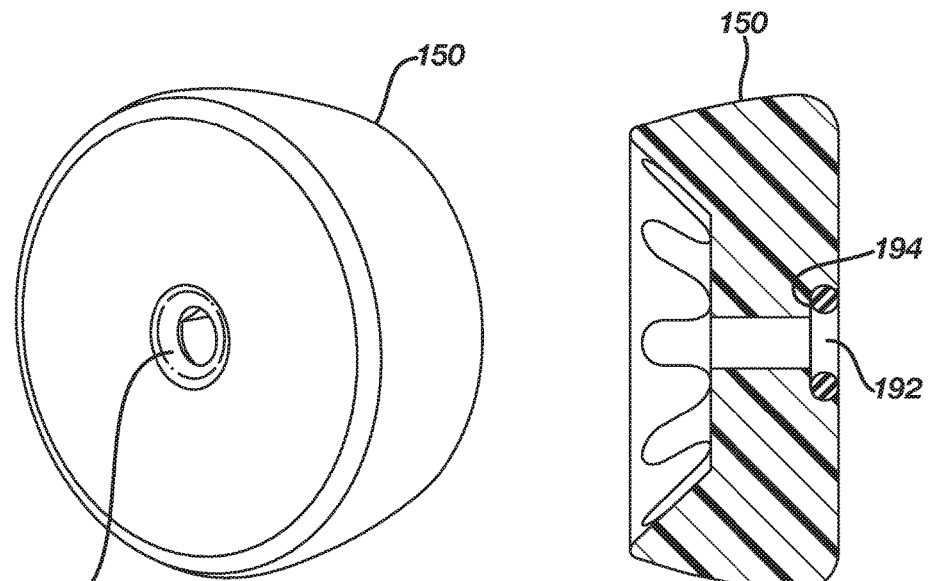

FIG. 5D illustrates another embodiment of the locking cap. The locking cap 150 includes an O-ring 192 in an O-ring recess 194 on the top of the locking cap 150. The O-ring 192 is configured to engage the cam portion 122 and may provide enough frictional force to fix the locking cap 150 to the driver 110. The O-ring 192 is placed in the O-ring recess 194 to fix the O-ring 192 to the locking cap 150. It is also possible that the O-ring 192 can fix the locking cap 150 in a position where the locking cap 150 does not engage the handle 110 without completely removing the locking cap 150 from the shaft 114. In other embodiments, the O-ring 192 may engage the shaft recess 122 to fix the locking cap 150 to the driver 110. In another embodiment, there may be a second shaft recess to fix the locking cap 150 in a position where the locking cap 150 does not engage the handle 110 without completely removing the locking cap 150 from the shaft 114.

Figure 5E:
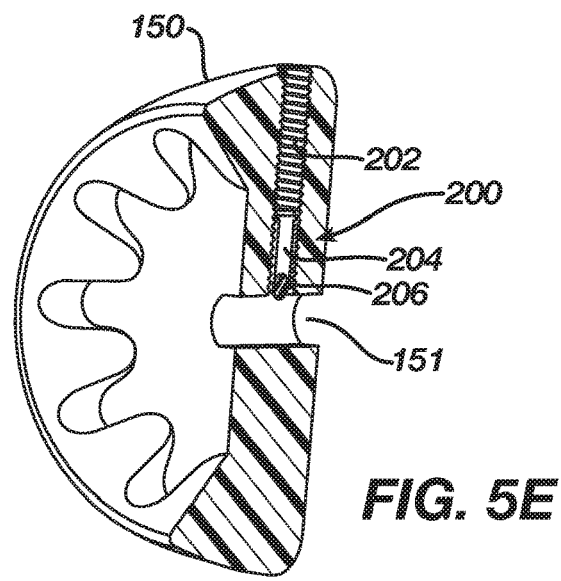

FIG. 5E illustrates another embodiment of the locking cap. The locking cap 150 includes a screw spring plunger 200. The locking cap 150 includes a screw hole 202 extending from the outer edge of the locking cap 150 to the through-hole 151. The screw spring plunger 200 includes a screw spring 204 and a plunger 206. The screw spring plunger 200 may be screwed into the screw hole 202 until the plunger 206 is in the through-hole 151. The screw spring 204 applies a biasing force to the plunger 206. The plunger 206 engages the shaft recess 126 to fix the locking cap 150 to the driver 110. In another embodiment, there may be a second shaft recess to fix the locking cap 150 in a position where the locking cap 150 does not engage the handle 110 without completely removing the locking cap 150 from the shaft 114.

Figure 5F:
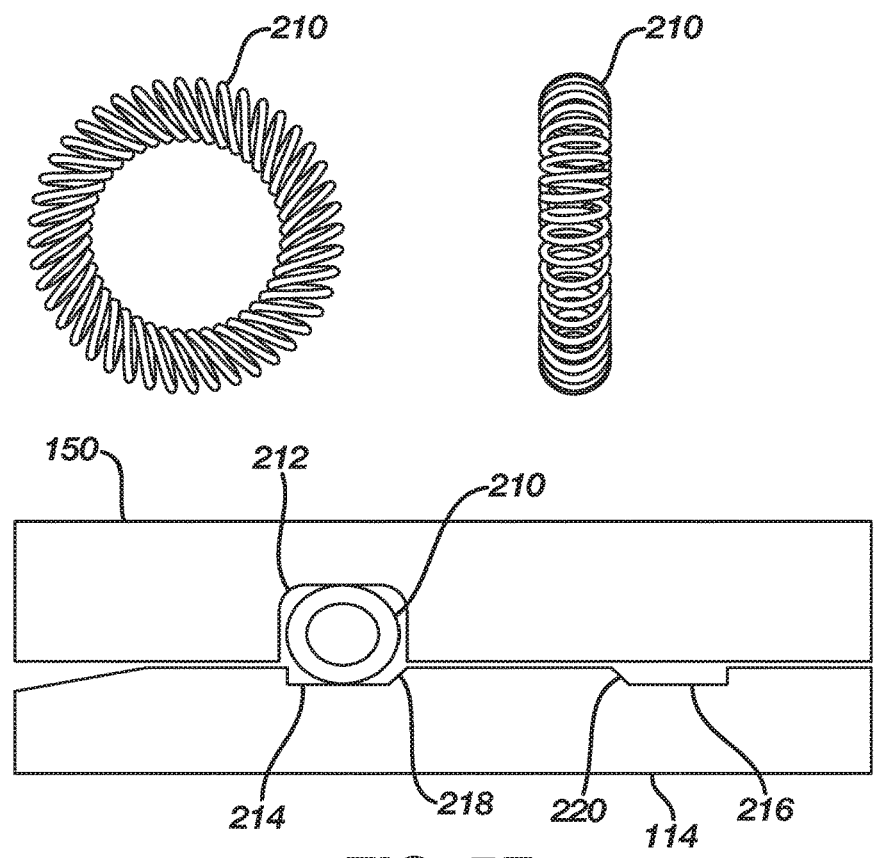

FIG. 5F illustrates another embodiment of the locking cap. The locking cap 150 includes a canted coil spring 210 in a canted coil spring recess 212. The canted coil spring 210 is configured to engage the first shaft recess 214 to fix the locking cap 150 to the driver 110. It is also possible that the canted coil spring 210 can engage the second shaft recess 216 to fix the locking cap 150 in a position where the locking cap 150 does not engage the handle 110 without completely removing the locking cap 150 from the shaft 114. The first shaft recess 214 may include first recess sloped surface 218 to facilitate sliding of the locking cap 150 to disengage the canted coil spring 210 from the first shaft recess 214. Likewise, the second shaft recess 216 may include second recess sloped surface 220 to facilitate sliding of the locking cap 150 to disengage the canted coil spring 210 from the second shaft recess 216.

Figure 6:
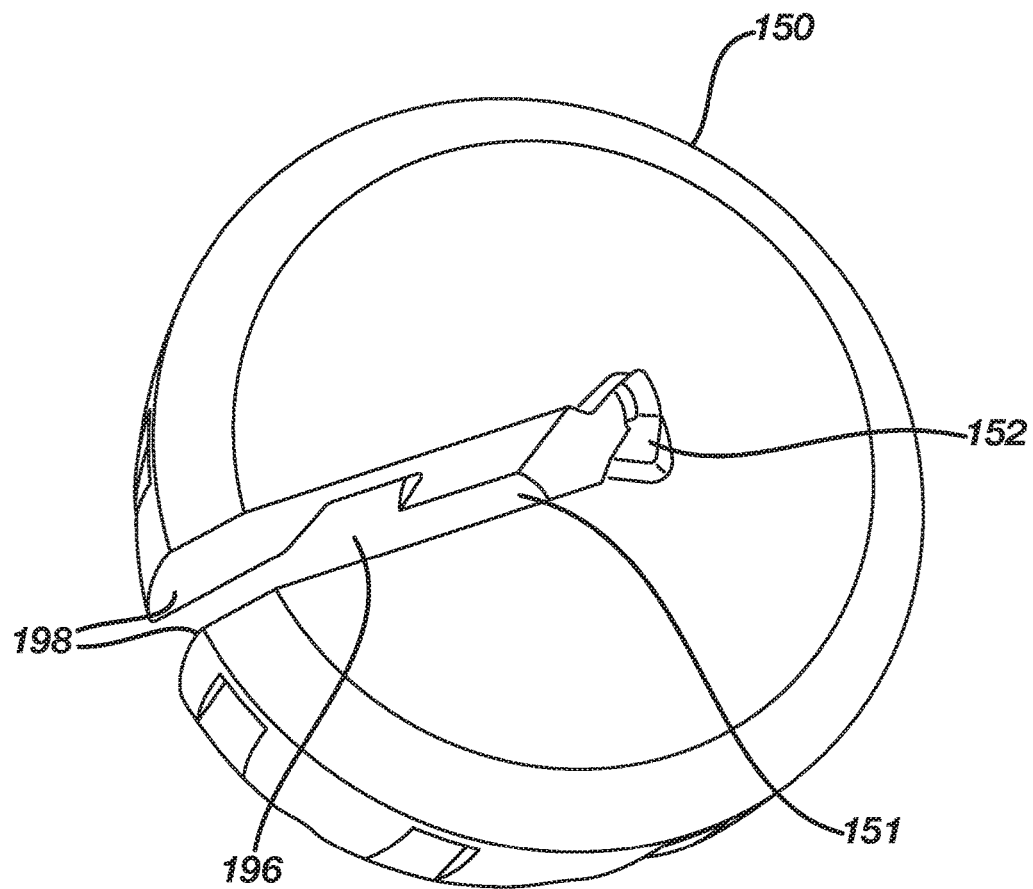
FIG. 6 illustrates another embodiment of the locking cap.

FIG. 6 illustrates another embodiment of the locking cap. This embodiment of the locking cap 150 includes a slot 196. The slot 196 allows for the locking cap 150 to be placed on the shaft 114 from direction substantially perpendicular to the shaft 114. The slot 196 includes a through hole 151 at the center of the locking cap 150 that engages the shaft 114 like the through hole described above with respect to FIGS. 2A-2G. In the embodiment shown in FIG. 6, there is a single snap arm 152 to engage the mating recess 153 on the shaft 114. Alternatively, there could be two snap arms positioned on either side of the through hole 151. The slot 196 also includes slot mating surfaces 198. The slot mating surfaces 198 may engage the locking cap engagement protrusion 116 on the handle 112. This engagement may facilitate locking the rotation between the handle 112 and the shaft 114.

In another embodiment, the locking cap 150 may have locking cap alignment protrusions. The end of the handle 112 would have a mating recess with scallops along the outer edge. The locking cap alignment protrusions and scallops would engage one another like in the embodiments described above. In other words, in this embodiment the location of the alignment protrusions and the scallops are switched between the locking cap 150 and the handle 112. The operation and the variations for this embodiment would be like those described above.

As seen in the various figures the locking cap 150 may smoothly mate with the handle. This provides a consistent point of view for the surgeon when using the torque limiting driver system 100. Further, the smooth mating makes the combined driver 110 and locking cap 150 appear like a single item.

The locking cap 150 may be manufactured from various known materials using various manufacturing techniques. The specific materials used and the specific shapes used should be sufficiently strong to provide the needed torque to a screw without any breakage of the locking cap 150 or other elements of the torque limiting driver system 100. Further, the torque at which a screw would break may provide an upper limit on the strength needed by the locking cap 150. In testing, it was found that some screws would fail when about 1.8 Nm of torque was applied. An embodiment of the locking cap was formed and tested, and the test locking cap was able to apply up to 4 Nm of torque, which means that a screw will fail before the locking cap. One method of manufacture includes injection molding. The various embodiments of the locking cap 150 described above lend themselves to the one piece construction accomplished by single shot injection molding. Various available materials and injection molding lend themselves to producing a strong but inexpensive molding cap. For example, glass reinforced polymer materials provide a cost effective and strong moldable material. An example of a suitable material may include glass-filled polyarylamide, such as IXEF® GS-1022 50% glass-filled polyarylamide available from Solvay.

The use of a locking cap 150 to lock the driver 110 provides a simple low cost solution to the situation where additional torque is needed when driving screws. The cost of a locking cap is less than an additional driver. Further, it may prevent the inadvertent use of the normal driver when the driving torque should be limited.

It should be appreciated by those skilled in the art that any diagrams or schematic drawings herein represent conceptual views of illustrative structures embodying the principles of the invention.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Further, various elements from the various embodiments may be combined to form other embodiments that are within the spirit and scope of the invention. Accordingly, the foregoing disclosure, description, and figures are for illustrative purposes only and do not in any way limit the invention, which is defined only by the claims.

What is claimed is:

1. A torque limiting driver system, comprising:
    a torque limiting driver including:
        a handle including a torque limiting mechanism, where the handle includes a locking cap engagement protrusion;
        a shaft with a cam portion including a cam mating feature; and
    a locking cap including:
        a mating recess including a plurality of scallops along the outer edge of the mating recess and wherein the plurality of scallops are configured to interface with the first mating feature;
        a through-hole with through-hole mating feature configured to interface with the cam mating feature, wherein
    the locking cap is configured to engage the torque limiting driver to lock the rotation of the shaft with respect to the handle;
    the shaft includes a shaft recess; and
    the locking cap includes a snap arm configured to engage the shaft recess such that the locking cap is fixed to the torque limiting driver.

2. The torque limiting driver system of claim 1, wherein the cam mating feature is a portion of the cam portion that has a flat portion and the through-hole mating feature has a flat portion complementary to the flat portion of the cam mating feature.

3. A torque limiting driver system, comprising:
    a torque limiting driver including:
        a handle including a torque limiting mechanism, where the handle includes a locking cap engagement protrusion;
        a shaft with a cam portion including a cam mating feature; and
    a locking cap including:
        a mating recess including a plurality of scallops along the outer edge of the mating recess and wherein the plurality of scallops are configured to interface with the first mating feature;
        a through-hole with through-hole mating feature configured to interface with the cam mating feature, wherein
    the locking cap is configured to engage the torque limiting driver to lock the rotation of the shaft with respect to the handle;
    the locking cap further includes external clips extending from an outer edge of the locking cap wherein the external clips are configured to engage the handle such that the locking cap is fixed to the torque limiting driver.

4. The torque limiting driver system of claim 3, wherein the cam mating feature is a portion of the cam portion that has a flat portion and the through-hole mating feature has a flat portion complementary to the flat portion of the cam mating feature.

\* \* \* \* \*